(12) United States Patent
Sabaria

(10) Patent No.: US 9,078,957 B2
(45) Date of Patent: Jul. 14, 2015

(54) METHODS OF POLYMERIC STENT SURFACE SMOOTHING AND RESURFACING TO REDUCE BIOLOGICALLY ACTIVE SITES

(75) Inventor: Patrick Sabaria, Saint Nom la Breteche (FR)

(73) Assignee: ARTERIAL REMOLDELING TECHNOLOGIES, S.A., Noisy le Roi (FR)

( * ) Notice: Subject to any disclaimer, the term of this patent is extended or adjusted under 35 U.S.C. 154(b) by 1011 days.

(21) Appl. No.: 12/282,752

(22) PCT Filed: Apr. 11, 2007

(86) PCT No.: PCT/IB2007/000941
§ 371 (c)(1),
(2), (4) Date: Sep. 12, 2008

(87) PCT Pub. No.: WO2007/116305
PCT Pub. Date: Oct. 18, 2007

(65) Prior Publication Data
US 2009/0095715 A1 Apr. 16, 2009

Related U.S. Application Data

(60) Provisional application No. 60/791,220, filed on Apr. 12, 2006, provisional application No. 60/814,533, filed on Jun. 19, 2006, provisional application No. 60/854,075, filed on Oct. 25, 2006.

(51) Int. Cl.
| | |
|---|---|
| *B44C 1/22* | (2006.01) |
| *A61L 31/10* | (2006.01) |
| *A61L 31/06* | (2006.01) |
| *A61L 31/14* | (2006.01) |

(52) U.S. Cl.
CPC ............... *A61L 31/10* (2013.01); *A61L 31/06* (2013.01); *A61L 31/148* (2013.01)

(58) Field of Classification Search
CPC ........ A61L 31/06; A61L 31/148; A61L 31/10
USPC .......................................................... 216/83
See application file for complete search history.

(56) References Cited

U.S. PATENT DOCUMENTS

| | | |
|---|---|---|
| 4,279,249 A | 7/1981 | Vert et al. |
| 5,957,975 A | 9/1999 | Lafont et al. |
| 6,120,847 A | 9/2000 | Yang et al. |
| 2004/0180131 A1 | 9/2004 | Cheng |
| 2005/0187615 A1 | 8/2005 | Williams et al. |
| 2006/0047336 A1* | 3/2006 | Gale et al. ............ 623/1.11 |
| 2007/0202147 A1* | 8/2007 | Kleiner et al. ........... 424/423 |

FOREIGN PATENT DOCUMENTS

EP   0 761 251 A1   3/1997

* cited by examiner

*Primary Examiner* — Duy Deo
*Assistant Examiner* — Mahmoud Dahimene
(74) *Attorney, Agent, or Firm* — Tarolli, Sundheim, Covell & Tummino LLP

(57) ABSTRACT

The present invention provides methods for fabricating a stent using a chemical treatment to smooth, polish or strengthen the stent. One such treatment involves exposing the stent to acetone or a similar solvent. In certain embodiments, the additional step comprises placing the stent in a bath containing acetone, or a similar solvent, where the bath also contains the polymer the stent is composed of. The acetone bath step may be conducted at a temperature that is below the glass transition temperature. The present invention also provides for methods of fabricating a stent using an acetone bath that comprises poly (lactic) acid. Other embodiments provide for methods of fabricating a stent using an acetone bath that comprises poly (lactic) acid and polyethylene glycol.

11 Claims, No Drawings

METHODS OF POLYMERIC STENT SURFACE SMOOTHING AND RESURFACING TO REDUCE BIOLOGICALLY ACTIVE SITES

CROSS-REFERENCE TO RELATED APPLICATIONS

This application claims priority to U.S. Provisional Application Ser. No. 60/791,220, filed on Apr. 12, 2006, 60/814,533, filed on Jun. 19, 2006 and 60/854,075, filed on Oct. 25, 2006, the entirety of each of which is incorporated herein by reference.

BACKGROUND OF THE INVENTION

The use of stents in various surgical, interventional cardiology, and radiology procedures has quickly become accepted as experience with stent devices accumulates and as the advantages of stents become more widely recognized. Stents are often used in body lumens to maintain open passageways such as the prostatic urethra, the esophagus, the biliary tract, intestines, and various coronary arteries and veins, as well as more remote cardiovascular vessels such as the femoral artery.

Stents are often used to treat atherosclerosis, a disease in which vascular lesions or plaques consisting of cholesterol crystals, necrotic cells, lipid pools, excess fiber elements and calcium deposits accumulate in the walls of an individual's arteries. One of the most successful procedures for treating atherosclerosis is to insert a deflated balloon within the lumen, adjacent the site of the plaque or atherosclerotic lesion. The balloon is then inflated to put pressure on and "crack" the plaque. This procedure increases the cross-sectional area of the lumen of the artery. Unfortunately, the pressure exerted also traumatizes the artery, and in 30-40% of the cases, the vessel either gradually renarrows or recloses at the locus of the original stenotic lesion. This renarrowing is known as restenosis.

A common approach to prevent restenosis is to deploy a metallic stent to the site of the stenotic lesion. Although metallic stents have the mechanical strength necessary to prevent the retractile form of restenosis, their presence in the artery can lead to biological problems including vasospasm, compliance mismatch, and even occlusion. Moreover, there are inherent, significant risks from having a metal stent permanently implanted in the artery, including erosion of the vessel wall. The stents may also migrate on occasion from their initial insertion location raising the potential for stent-induced blockage. Metal stents, especially if migration occurs, cause irritation to the surrounding tissues in a lumen. Also, since metals are typically much harder and stiffer than the surrounding tissues in a lumen, this may result in an anatomical or physiological compliance mismatch, thereby damaging tissue or eliciting unwanted biologic responses. In addition, the constant exposure of the stent to the blood can lead to thrombus formation within the blood vessel. Stents also allow the cellular proliferation associated with the injured arterial wall to migrate through the stent mesh, where the cells continue to proliferate and eventually lead to the narrowing of the vessel. Further, metal stents typically have some degree of negative recoil. Finally, metallic stents actually prevent or inhibit the natural vascular remodeling that can occur in the organism by rigidly tethering the vessel to a fixed, maximum diameter.

Because of the problems of using a metallic stent, others have recently explored use of bioabsorbable and biodegradable materials stents. The conventional bioabsorbable or bioresorbable materials from which such stents are made are selected to absorb or degrade over time. This degradation enables subsequent interventional procedures such as restenting or arterial surgery to be performed. It is also known that some bioabsorbable and biodegradable materials tend to have excellent biocompatibility characteristics, especially in comparison to most conventionally used biocompatible metals. Another advantage of bioabsorbable and biodegradable stents is that the mechanical properties can be designed to substantially eliminate or reduce the stiffness and hardness that is often associated with metal stents. This is beneficial because the metal stent stiffness and hardness can contribute to the propensity of a stent to damage a vessel or lumen. Examples of novel biodegradable stents include those found in U.S. Pat. No. 5,957,975, which is incorporated by reference in its entirety.

There are, however, still problems with many biodegradable stents. For instance, it has been found that continued exposure of a stent to blood can lead to undesirable thrombus formation. In particular, stents with irregular or sharp surfaces are undesirable because blood particles accumulate in the irregular surfaces, thereby accelerating thrombus formation. There therefore still exists a problem of limiting surface reactivity of the stent.

Accordingly, it is desirable to manufacture stents with few irregular or sharp surfaces. It is also desirable to reduce or eliminate reactive amino groups, which would reduce or eliminate platelet adhesion. The inventors have found a novel method to make a stent that result in decreased irregular and sharp edges and reduced platelet adhesion.

SUMMARY OF THE INVENTION

The present invention provides methods for fabricating a stent using a chemical treatment to smooth, polish or strengthen the stent. One such treatment involves exposing the stent to acetone or a similar solvent. The inventors have determined that they can create a superior stent by adding this additional step alone, or in conjunction with other treatments, to the stent fabrication process. In certain embodiments, the additional step comprises placing the stent in a bath containing acetone, or a similar solvent, where the bath also contains the polymer the stent is composed of. The acetone bath step is generally conducted at a temperature that is below the glass transition temperature. Preferably, the acetone bath step is conducted at a temperature of below 65° C., more preferably below 60° C., most preferably below 55° C. In certain embodiments, a temperature of about 25° C. is most preferred.

The additional step results in a decrease in the surface reactivity of the stent. Surprisingly, addition of this step helps to polish the sharp surfaces and irregularities created during manufacturing. While not wishing to be limited by any particular theory, the inventors believes this manufacturing process will provide a reduction or elimination of platelet adhesion or any blood elements involved in triggering thrombus formation by reducing or eliminating reactive amino groups.

The present invention also provides for methods of fabricating a stent using an acetone bath that comprises poly (lactic) acid. Other embodiments provide for methods of fabricating a stent using an acetone bath that comprises poly (lactic) acid and polyethylene glycol.

DETAILED DESCRIPTION

Definitions

"Bioresorbable polymer" as used herein refers to a polymer whose degradation by-products can be bio-assimilated or excreted via natural pathways in a human body.

"Acetone bath" as used herein refers to a bath comprising one or more solvents, where the solvents may be acetone, chlorinated hydrocarbons, and/or ketones. The polymeric stent fabrication method includes partially or fully immersed the polymeric stent into the acetone bath.

"Crimping" as used herein refers to a process that involves radial pressing on a polymeric cylindrical device having slits, or openings in the wall thereof to allow a decrease in the diameter of the device without substantially affecting the thickness of the wall or struts of the cylindrical device. Such process, typically also results in an increase in length of the cylindrical device.

"Degradable polymer" or "biodegradable polymer" as used herein refers to a polymer that breaks down into monomers and oligomers when placed in a human body or in an aqueous solution and maintained under conditions of temperature, osmolality, pH, etc., that mimic physiological media preferably without involving enzymatic degradation to minimize the risk of triggering the antigen antibody defense system of the human body.

"Final predetermined shape and diameter" as used herein refers to the desired diameter, length, design and wall thickness of a stent that has been deployed to a target site in a vessel, particularly a blood vessel, duct, or tube in a mammalian subject, particularly a human subject.

"Negative recoil" as used herein refers to an undesirable decrease in the size or diameter of an expanded stent after initial deployment.

"Positive recoil" as used herein refers to an increase in the size or diameter of a stent that has been educated to have a desired final diameter but has not been fully expanded to the desired final diameter.

"Relaxation-related recoil" as used herein refers to the slow change in dimensions of a polymeric device due to a time-dependent slow rearrangement of molecule conformations according to a well-known behavior of viscoelastic polymeric matters. Such rearrangement is due to thermal agitation that slowly leads the polymeric material to a thermodynamic equilibrium typical of the storage conditions when it has been processed under different environmental conditions. Relaxation is very slow below Tg, i.e., when the matter is in the glassy state.

"Tg" or "glass transition temperature" as used herein refers to the temperature at which a polymer changes from a rubbery state to a glassy state and vice versa.

The present invention provides methods for fabricating a stent using a chemical treatment to smooth, polish and/or strengthen the stent. The inventors have determined that they can create a superior stent by adding one or more additional treatment steps to the stent fabrication process. The treatment can use a gas or vapor of solvents, preferably acetone, especially a vapor with a linear flow rate over the stent. The additional step could also comprise placing the stent in a bath containing solvents, preferably acetone, where the bath also contains the polymer the stent is composed of. For bath treatments, the step is generally conducted at a temperature that is below the glass transition temperature. Preferably, the bath step is conducted at a temperature of below 65° C., more preferably below 60° C., most preferably below 55° C. In certain embodiments, a temperature below about 50° C. is most preferred.

The additional step or steps results in a decrease in the surface reactivity of the stent. Surprisingly, addition of this step helps to polish the sharp surfaces and irregularities created during manufacturing. While not wishing to be limited by any particular theory, the inventors believes this manufacturing process would reduce or eliminate platelet adhesion by reducing or eliminates reactive amino groups.

The present invention also provides for methods of fabricating a stent using an acetone bath that comprises poly (lactic) acid. Other embodiments provide for methods of fabricating a stent using an acetone bath that comprises poly (lactic) acid and polyethylene glycol.

I. Exemplary Stent Fabrication and Properties

The stents may be formed from any biodegradable, biocompatible, bioresorbable polymer, preferably a thermoplastic polymer. As used herein, a bioresorbable polymer is one whose degradative products are metabolized in vivo or excreted from the body via natural pathways. Preferably, the stent of the present assembly is formed from a degradable and bioresorbable polymer having a Tg at least 8 degrees above 37° C., preferably at least 20 degrees above 37° C. The polymer of the stent can be a homopolymer or a copolymer. Preferably, the stent is formed from a thin layer of one or more amorphous, bioresorbable polymers, i.e., the polymers used to form the stent preferably are not crystalline. It is also preferred that the polymers used to form the stent do not generate crystalline residues upon degradation in vivo. It is also contemplated that the chains of the polymer may be or may not be cross-linked. Light cross-linking, however, is acceptable if thermal and viscoelastic characteristics that allow education, crimping, and deployment of the device are sufficiently maintained.

Appropriate biodegradable polymers may include, but are not limited to, poly (L-lactide), polyglycolide, poly (D, L-lactide), copolymers of lactide and glycolide, polycaprolactone, polyhydroxyvalerate, polyhydroxybutyrate, polytrimethylenecarbonate, polyorthoesters, polyanhydrides, and polyphosphazenes. Examples of the types of polymers that are suitable for the stent of the present invention include, but are not limited to, lactic acid-based stereocopolymers (PLAx copolymers composed of L and D units, where X is the percentage of L-lactyl units) ($55<Tg<60$), copolymers of lactic and glycolic acids (PLAxGAy, where X, the percentage of L-lactyl units, and Y, the percentage of glycolyl units, are such that the Tg of the copolymer is above 45° C.), and Poly(lactic-co-glycolic-co-gluconic acid) where the OH groups of the gluconyl units can be more or less substituted (pLAx-GayGLx, where X, the percentage of L-lactyl units, and Y, the percentage of glycolyl units, and Z the percentage of gluconyl units are such that the Tg of the terpolymer is above 45° C.). Other suitable polymers include, but are not limited to, polylactic acid (PLA), polyglycolic acid (PGA) polyglactin (PLAGA copolymer), polyglyconate (copolymer of trimethylene carbonate and glycolide, and a copolymer of polyglycolide or lactide acid or polylactic acid with ε-caprolactone), provided that the polymer has a glass transition temperature, Tg, of at least 45° C. or greater.

In one preferred embodiment, the stent comprises a polylactic acid stereocopolymer produced from L and DL lactides. The polymer is designated herein as "PLAX" where X represents the percentage of the L-lactic acid units in the mixture of monomers used to prepare the lactides. Preferably X is in the range of 10 to 90, more preferably 25 to 75. In another preferred embodiment, the stent comprises a polylactic acid, glycolic acid copolymer produced from L and DL lactides and glycolides. The polymer is designated herein as "PLAXGAY" where Y represents the percentage of glycolic acid units in the mixture of monomers used to prepare the copolymers. Preferably, the copolymers do not contain glycolyl repeating units since such units are known to be more inflammatory than lactyl repeating units. Preferably, the polymers are prepared using Zn metal or Zn lactate as initiator. To ensure good initial mechanical properties of the stent, the molecular weight of the polymer in the region having the second in vivo lifetime is preferably above 20,000 daltons, more preferably 100,000 daltons or larger. The polydispersity, I=Mw/Mn, is preferably below two and should not greatly reflect the presence of low molecular weight oligomers smaller than 2,000 daltons as determined by size exclusion chromatography.

Optionally, the polymeric layer used to make the stent impregnated with an anticoagulant agent, such as heparin, anti-oxidants, such as vitamin E, compounds that regulate cellular proliferation, or anti-inflammatory drugs, such as corticosteroids, to provide localized drug delivery. Such drugs are incorporated into the polymeric layer using techniques known in the art. Agents may also be incorporated into the base polymer that forms the body of the stent, as long as the incorporation does not have significant adverse effects on the desired physical characteristics of the stent such as during radial stent deployment and degradation time. For intravascular stents, it is preferred that the film has a thickness of from about 0.05 mm to 0.2 mm.

Further, in some embodiments, the stent may be coated with or the polymer of the stent may comprise compounds that modulate wound healing. Generally, compounds that modulate wound healing may be any compound that cross links with fibrin to provide matrix for cell, especially endothelial cells, adhesion and migration; functions as an early component of the extracellular matrix or assists in matrix formation; binds to collagen and interacts with matrix glycosaminoglycans; has chemotactic properties for macrophages, fibroblasts cell, endothelial cells, smooth muscle cells and epidermal cells; substances which effect the structure and function of the cytoskeleton and encourage cell migration, especially endothelial cells; promotes opsonization and phagocytosis; forms a component of the fibronexus; forms scaffolding for collagen deposition; or functions otherwise to promote healing.

Examples of compounds that promote wound healing include, but is not limited to, proteases; vasoactive substances such as serotonin and histamine; fibronectin; collagenases; plasminogen activator; neutral proteases; elastin; collagens; proteogycans such as chondroitin-4-sulfate, dermaten sulfate and heparin sulfate; sulfated and non-sulfated glycosaminoglycans; epidermal growth factor (EGF); hormones such as estradiol, testosterone or progesterone; macrophage derived growth factor (MDGF); platelet derived growth factor (PDGF); thrombin; insulin; certain lymphokines; vascular endothelial growth factor (VEGF); fibroblast growth factors; co-factors such as iron, copper, and vitamin C; adrenomedullin; angiogenin; angiopoietin-1; angiopoitin-related growth factor; brain derived neurotrophic factor; corticotropin-releasing hormone; Cyr16; erythropoietin; follistatin; hepatocyte growth factor; interleukins (IL-3, IL-8); midkine; neurokinin A; neuropeptide Y (NPY); pleiotrophin; progranulin; proliferin; secretoneurin; substance P; transforming growth factor; VG5Q; factors that recruit pericytes; and becaplermin.

It is contemplated that the stent may be made by any method. In one preferred embodiment, the stent is a formed from a biodegradable polymeric band comprising a head having a slot and a tongue comprising a catch or locking mechanism proximate the longitudinal edge thereof. The cylindrical element, which has an inner and outer surface, is formed by inserting a portion of the tongue through the slot to provide a cylindrical element having a first reduced diameter configuration. Following deployment, the cylindrical element is in a second expanded diameter configuration wherein the distal catch mechanism engages the inner surface of the head and prevents radial collapse or recoil of the polymeric stent. In a second preferred embodiment, the stent is formed from a plurality of interconnected polymeric bands each of which comprises a head having a slot and a tongue comprising a catch mechanism proximate the longitudinal edge thereof.

In one embodiment, the stent is formed by laser cutting of a cylindrical tube. In another embodiment, the stent is formed by laser cutting a flat polymeric sheet in the form of the stent, and then rolling the pattern into the shape of the cylindrical stent and providing a longitudinal weld to form the stent. In another embodiment, the stents are created by chemically etching a flat polymeric sheet and then rolling and welding it to form the stent, or coiling a polymeric wire to form the stent.

In another preferred embodiment, the stent may also be formed by molding or injection molding of a thermoplastic or reaction injection molding of a thermoset polymeric material. For instance, in one embodiment, a polymeric material is poured into a mold to form a two dimensional grid. The flat grid is then rolled and extremities are welded or glued to form a cylinder. In other embodiments, the polymeric material is injected into a three dimensional mold to form the cylindrical stent. Further, filaments of the compounded polymer may be extruded or melt spun. These filaments can then be cut, formed into ring elements, welded closed, corrugated to form crowns, and then the crowns welded together by heat or solvent to form the stent. Lastly, hoops or rings may be cut from tubing stock, the tube elements stamped to form crowns, and the crowns connected by welding or laser fusion to form the stent.

Generally, the struts are arranged in patterns that are designed to contact the lumen walls of a vessel and to maintain patency of the vessel thereby. A myriad of strut patterns are known in the art for achieving particular design goals.

It is contemplated that a crimped stent may incorporate slits or open spaces to allow for the temporary reduction in diameter of the cylindrical tube without substantially altering the wall thickness. Moreover, a stent embodying the present invention can include teeth and corresponding catching structure that operates to maintain an expanded form. Moreover, polymer based stents embodying structure defined by a wire or ribbon coil or helix or a knitted mesh configuration are possible examples of self-expanding stents. Other important design characteristics of stents include radial or hoop strength, expansion ratio or coverage area, and longitudinal flexibility. One strut pattern may be selected over another in an effort to optimize those parameters that are of importance for a particular application.

It is also contemplated that the biodegradable stent may have a programmed pattern of in vivo degradation. Stent polymeric structure allows for differential speed degradation. See, for example, U.S. Pat. No. 5,957,975, the entirety of which is incorporated by reference. In one embodiment, the stent comprises at least one substantially cylindrical element having two open ends and a plurality of regions circumferentially spaced around the cylindrical element and extending from one open end to the other open end of the cylindrical element. Each of the regions is configured or designed to have a desired in vivo lifetime. At least one of the regions is designed to have a shorter in vivo lifetime than the other region or regions. This means that the region having the shorter in vivo lifetime degrades sooner after deployment than the regions having a longer in vivo lifetime. Thus, when stents designed in accordance with the present invention are deployed within the lumen of a vessel of a patient, the cylindrical element acquires one or more fissures which extend from one open end of the cylindrical element to the other open end of the cylindrical element within a desired, predetermined period of time after the stent is deployed in the patient. It has been determined that such dismantling, or fragmentation, within a predetermined period of time after deployment allows for enlargement of the lumen of the vessel via the process of arterial remodeling.

Example I

The regions of the stent with the different in vivo lifetimes can be made in a variety of ways. Preferably, such stents are made by producing regions having a first in vivo lifetime, i.e., a shorter in vivo lifetime, in a polymeric layer having the predetermined second, or longer, in vivo lifetime. The regions having the first in vivo lifetime are produced by heating the respective regions of the polymeric layer having a second in vivo lifetime for a time and at a temperature sufficient to cause local partial degradation of the polymeric chains. Such treatment, which can be accomplished using a piloted hot needle, laser beam, or flow of hot air, renders the polymer in the heated region more sensitive to hydrolytic degradation. Alternatively, the regions having a first in vivo lifetime may be produced in a polymeric layer having a second in vivo lifetime by incorporating a sufficient number of acidic ions into the respective regions of the polymeric layer. Preferably, the acidic ions are provided by compounds that are not soluble in blood.

Example II

Regions having a first in vivo lifetime can also be produced in a polymeric film having a second in vivo lifetime by exposure of the respective regions to beta radiation or gamma radiation for a sufficient time to induce partial cleavage of the polymeric chains within the respective regions. Provided the polymeric layer has a thickness of less than 0.3 mm, regions having a first in vivo lifetime can also be produced in a polymeric film having a second in vivo lifetime by introducing areas of mechanical weakness into the polymer. One method of introducing mechanical weakness is by reducing the thickness of the polymer in the respective region or forming holes therein. Regions having a first in vivo lifetime can also be produced in a polymeric film having a second in vivo lifetime by applying mechanical stress to the respective region. However, this latter process is difficult to control and, thus, is less preferred. Differing lifetimes can also be created by providing one or more different coatings over different regions of the biodegradable stent.

Example III

Another method for producing a polymeric layer in which one region or a plurality of spaced apart regions have a first in vivo lifetime and other regions have a second in vivo lifetime is to incorporate strips or fibers of a faster degrading bioresorbable polymer into a film made from a slower degrading polymer. For example, a mesh or a parallel array of fibers or strips of PGA or any other faster degrading bioresorbable polymer can be embedded into the respective regions of a polymeric film of PLA that may be designed to be slower degrading. Embedding can be achieved by inserting the mesh or fibers between two melted sheets of the slower degrading polymer. Provided the relative solubilities are compatible, the fibers or mesh can be placed in an organic solution of the slower degrading polymer and the desired polymeric film formed by evaporation of the organic solvent. One example of a method for embedding a mesh made from one polymer into a polymeric layer made from a second polymer is described in U.S. Pat. No. 4,279,249 issued to Vert et al. on Jul. 21, 1981, which is specifically incorporated herein by reference. A stent having the desired shape and orientation of regions is then formed from the polymeric layer by standard techniques such as stamping, employing a laser beam, or any other technique used in the art to tool a polymeric film.

The initial polymeric cylindrical device that is formed by any of these processes can be configured to have the final predetermined shape, length, wall thickness and diameter, all of which are tailored to the application for which the stent is to be utilized. For example, for cardiovascular applications the initial polymeric device that is formed by these processes can have a final predetermined length ranging from 0.5 cm to approximately 3 cm. For certain applications, the initial polymeric cylindrical device can have a final, predetermined diameter ranging from 0.50 mm to 8.0 mm with a final, predetermined wall thickness ranging from 0.05 to 0.5 mm. Alternatively, the initial cylindrical device that is formed by any of these processes can have a smaller diameter than the final predetermined diameter.

In those instances where the initial polymeric cylindrical device has a smaller diameter than the final predetermined diameter, slits or openings are formed in the cylindrical device as described above, and then the cylindrical device is deformed or expanded to the final shape and diameter. This can be achieved by inserting an expandable device such as a balloon into the stent.

Once the stent is formed, the stent is immersed in a bath comprising at least acetone and then dried. To their surprise, the inventors found that immersing the stent in the bath had the unexpected result of decreasing the sharp surfaces and irregularities, as determined by scanning electron microscopy. The stents can be dried by any means, but preferably, the stents are dried at atmospheric pressure until they achieve a constant weight. Complete drying may be verified by measuring the residual acetone by gas chromatography or by thermo gravimetric analysis.

Example IV

The total time that the stent is immersed in the bath is critical as the acetone bath can potentially dissolve the stent. In this embodiment, the stent is totally immersed in the bath for 0.5 seconds.

In other embodiments, the stent is immersed in the bath for at least about 0.1 second, preferably up to 1 second. It is also contemplated that the total immersion time may be used as another method to alter the in vivo lifetime of one or more sections of the stent.

The acetone bath step is generally conducted at a temperature that is below the glass transition temperature of the polymer that forms the stent. Preferably, the acetone bath step is conducted at a temperature of below 65° C., more preferably below 60° C., most preferably below 55° C. In certain embodiments, a temperature below about 50° C. is most preferred. It is preferable to use a temperature that is below the glass transition temperature of the stent as this results in reducing the exposure of the stent to adverse temperature conditions.

If the surface tension of the solvent used in the solvent bath is too high, it may inhibit solvent entry into the inner surface of the stent, leading to variation in the properties of the stent over its length. If desired, this can be avoided by manipulation of the atmospheric pressure over the solvent bath, adding agents to the bath to reduce the surface tension of the solvent, agitation or altering flow through the lumen of the stent.

The acetone concentration in the bath can be any concentration determined by one skilled in the art to decrease the sharp edges and irregularities of the stent, decrease the surface reactivity of the stent, and/or decrease the reactive amino groups. It is preferred that the polymer dissolved in the acetone bath has a concentration of at least about 0.05% weigh/volume, and is most preferably at least about 5% weight volume.

In addition, certain embodiments of the invention provide for the addition of poly (lactic) acid (PLA), poly-L-lactide, poly-DL-lactide, L-lactide monomers and/or DL-lactide monomers to the acetone bath. It is further contemplated to add one or more polyethers to the acetone bath. It is contemplated that the polyethers may include, but is not limited to, polyethylene glycol, polyethylene oxide, crown ethers, or mixes thereof. Preferably, the polyether added to the acetone bath is polyethylene glycol (PEG). In one preferred embodiment, the acetone bath contains PLA-PEG diblock copolymers. The concentration of PLA and/or PLA-PEG diblock copolymers is greater than about 0.1% weight/volume, preferably greater than about 10% weight/volume, and more preferably about 5% weight/volume. It is also understood that the acetone bath may contain other polymers, compounds and/or chemicals that are also included in the composition of the stent. For instance, if the stent polymer contains a biodegradable polymer such as polycaprolactone, polyglycolide, poly-3-hydroxybutyrate, polyglycolide, poly (D, L-lactide), copolymers of lactide and glycolide, polycaprolactone, polyhydroxyvalerate, polyhydroxybutyrate, polytrimethylenecarbonate, polyorthoesters, polyanhydrides, polyphosphazenes, or mixes thereof, the polymer(s) may also be added to the acetone bath.

Further, it is contemplated that other solvents may be used instead of acetone or may be included with the acetone in the bath. For instance, solvents that may be used in the bath includes one or more types of chlorinated or halogenated hydrocarbons. The chlorinated hydrocarbons contemplated includes, but is not limited to: dichloromethane, 1,1,1-trichloroethane, 1,1,2-trichloroethane, 1,1-dichloroethane, trichloroethylene, lindane, polychlorinated biphenyls, dioxins, furans, perchloroethylene, chloroform, methoxychlor, hexachlorocyclohexane, chlordane, dieldrin, heptachlor, methoxychlor, toxaphene, carbon tetrachloride, or mixtures thereof.

It is also contemplated to use solvents from the ketone family instead of acetone or included with acetone in the bath. Members of the ketone includes organic compounds that contain a carbonyl group that is bonded to only carbon atoms. The ketones contemplated includes, but is not limited to: acetoacetate, acetophenone, butanone, C-11 ketone, cyclohexanone, diacetone alcohol, diisobutyl ketone, isophorone, methyl amyl ketone, methyl ethyl ketone, methyl isoamyl ketone, methyl isobutyl ketone, beta-hydroxybutyrate, or mixes thereof. Other useful solvents and mixtures thereof that can be utilized in the baths include the aldehydes, which could also help to stabilize certain polymers used in the stents. In some embodiments, drugs or compounds that modulate coagulation or wound healing may be added to the bath.

Further, the step of the acetone bath can occur at any point during the fabrication of the stent. Preferably, the step of the acetone bath occurs at the end of the stent fabrication. More preferably, the step of the acetone bath occurs before the stent is educated.

II. Exemplary Educating and Crimping of the Stent

While it is at the final predetermined shape, size, and diameter, the cylindrical device is educated by heating the device to a temperature above the Tg of the polymer from which the device is formed. The device is heated for a time sufficient to erase former process-related memory and to impart a new memory of the final predetermined shape and diameter to the polymeric cylindrical device. It is believed that such conditions allow the polymer chains to relax and reorganize themselves from an entanglement typical of the former processing stages to an entanglement typical of the high temperature at which the cylindrical device is compatible with the final or deformed shape and size. When the polymeric cylindrical device has an initial diameter that is less than the final predetermined diameter, it is desired to heat to a temperature well above the Tg of the polymer. This heating step erases the anisotropic stresses promoted by the extrusion or molding process and the former processing-related memory of the polymer chains. Good results have been obtained by heating a laser-precut polymeric cylindrical device formed from PLA75 and deformed from a diameter of 1.0 mm to 4 mm at a temperature of 80° C. for 30 minutes. Temperatures of from about 45° C. to about 120° C. and times of 5 minutes or more should be suitable for educating stents made from PLAx with $0<X<100$, PLAxGAy with $0<X<25$ and $75<Y<100$, or any PLAxGAyGLz.

The polymeric cylindrical device is then crimped. "Crimping" as used herein refers to a process that involves radial pressing on a polymeric cylindrical device having slits, or openings in the wall thereof to allow a decrease in the diameter of the device without substantially affecting the thickness of the wall or struts of the cylindrical device. Such process may also result in an increase in length of the cylindrical device.

To crimp the educated cylindrical device, it is mounted onto a device with a smaller diameter. The diameter of the educated cylinder is reduced by heating the cylinder to a temperature below the Tg of the polymer while evenly applying pressure on the exterior surface of the wall of the cylindrical device.

In some embodiments, the polymeric stent is crimped onto an inflatable device such as an inflatable balloon catheter. In this instance, the stent assembly after crimping comprises an inflatable balloon catheter and an expandable, educated, polymeric stent snugly and stably disposed thereon. Slits or open spaces that allow for a reduction in diameter of the cylindrical device without substantially altering the wall thickness during crimping are incorporated into the cylindrical device prior to the time the cylindrical device is crimped on the inflatable balloon catheter. The temperature at which the cylindrical device is heated during crimping is high enough to allow reduction in diameter of the cylindrical device but low enough to not erase the memory of the final predetermined shape and diameter of the educated cylindrical device. Ideally, the temperature is less than the glass transition state of the polymer. More preferably, the temperature is at about 50° C. Thus, the temperature at which the educated cylindrical device is heated during crimping is less than the temperature at which the cylindrical device is heated during education of the cylindrical device. Further, the time it takes to crimp the educated cylindrical device can vary, depending upon the temperature, size and composition of the stent In accordance with the present method, expansion of the polymeric stent can be achieved by any means. In one embodiment, a balloon is used merely as a carrier for the stent through the body. In this preferred embodiment, the stent expansion occurs by the positive recoil properties of the stent; thus, the expansion is balloon inflation independent. In another preferred embodiment, a balloon is inflates and/or heated to initiates the stent expansion. It is contemplated that the positive recoil properties of the stent expand the stent to its final predetermined diameter. The temperature used to initiate the stent expansion may be any temperature at or below the Tg of the polymer; preferably the temperature is about body temperature. In a less preferred embodiment, a balloon is inflated to expand the polymeric stent to its final predetermined shape.

In another aspect, the method of the present invention starts with a polymeric tube whose diameter initially is less than the final predetermined diameter. Such tube is first heated to a temperature close to or above the Tg of the polymer and expanded to provide a cylindrical device whose diameter is equal to the final desired diameter. Thereafter the cylindrical device is educated as described above to provide an educated cylindrical device having a memory of the final predetermined shape and diameter, and then crimped on a balloon catheter as described above to provide an assembly comprising the balloon catheter and an expandable, educated, polymeric stent snugly and stably disposed thereon.

The present invention also provides an assembly comprising an inflatable balloon catheter and a polymeric stent prepared in accordance with the present method.

Preferably, the stent of the present invention exhibits little to no relaxation-related negative recoil when deployed in the blood vessel of a subject. Advantageously, the assembly of the present invention has a diameter that allows it to be easily inserted into a blood vessel of the subject and advanced to a target site. Preferably, the stent of the present invention exhibits expansion (positive recoil) and adaptation to the geometry of the artery when the stent is not fully deployed up to its final diameter during deployment. Positive recoil over several days will create outward radial pressure for long periods of time. This outward radial pressure aids in positive vascular remodeling by assisting stabilizing the injured artery or vulnerable plaque, assist in cellular progress to repair injury of original acute expansion, assist in security of tissue flaps, and the like.

In addition, the stent of the present invention is stably disposed on the balloon, meaning that a mechanical restraint is not required to prevent the stent from rapidly expanding to its final diameter during storage at room temperature. Thus, although not required, the assembly of the present invention, optionally, also comprises a retractable sheath covering the exterior surface of the stent. Such sheath serves to prevent deformation of the stent and preclude or slow expansion during storage.

III. Exemplary Procedures For Determining Times and Temperatures For Educating and Crimping the Stent of the Present Invention Temperatures and times suitable for educating the cylindrical device and for thereby developing a stent that resistant to negative recoil, and in fact has positive recoil, can be assessed by first crimping the stent of the present invention onto a balloon catheter. The balloon is then inflated to initiate stent expansion. The balloon is removed and the stent is stored at 37° C. While in storage, the stent may increase in diameter because of the positive recoil properties of the stent. If the stent exhibits little to no negative recoil when stored under these conditions for 4 to 6 weeks or, preferably the time estimated for an artery wall to recover from PTC angioplasty, the times and temperatures employed for educating the stent are suitable. In those cases where the polymeric stent exhibits a small amount of recoil, the cylindrical device is preferably educated at a diameter slightly larger than the final predetermined diameter to compensate for the small amount of negative recoil.

Temperatures and times suitable for crimping the stent to a reduced diameter can be assessed by allowing the stent-mounted balloon catheter of the present assembly to stay at room temperature or at the storage temperature. If the crimped stent stays collapsed at the small diameter corresponding to the deflated balloon under these conditions, the times and temperatures employed during crimping are suitable.

Optimization of the imparted stent mechanical properties such as positive recoil can be achieved by storing the finished product at a room temperature below 20° C. Preferably, the finish product is refrigerated at about 6° to 8° C.

IV. Deployment of the Stent

The polymer-based stent is first preheating for a period of 3 to 6 min at around 37° C. The preheating of the stent can occur by any means, including heating in saline, the in vivo blood stream, or hot air. After the preheating period, the polymer-based stent assembly of the present invention is introduced into a duct, tube, or vessel, e.g. a blood vessel of a mammalian subject, preferably in conjunction with a guiding catheter, and advanced to a target site, e.g., the site of stenotic lesion. After it is located at the target site the balloon is rapidly inflated to initiate expansion of the stent. Alternatively, the stent may be placed on a deployment device that is capable of localized heating of the stent when the stent is correctly positioned. During this process the diameter of the stent increases, but the thickness of the walls of the stent remain substantially the same.

It is further contemplated that fracturing of the plaque and deployment of the stent may be done concurrently. If a balloon is used in such cases, the balloon is inflated to a pressure of about 8 to 12 atmospheres to crack the plaque and expand the stent. Alternatively, the vessel may be pre-dilated using angioplasty without the stent. Thereafter, the stent is introduced into the desired site on a separate catheter, preferably an expanding balloon catheter.

In addition to coronary arteries, the present stent may be used in other arteries such as for example, femeroiliac arteries, the carotid artery, vertebro-basilar arteries, as well as in the interior of other hollow passageways such as for example veins, ureters, urethrae, bronchi, biliary and pancreatic duct systems, the gut, eye ducts, and spermatic and fallopian tubes. Indeed, it is further contemplated that certain aspects of the present invention include devices that are used as substitutes for veins, arteries, and ductal or tubal structures in the body.

While only the presently preferred embodiments have been described in detail, as will be apparent to those skilled in the art, alternatives, additions, modifications and improvements maybe made to the device and method disclosed herein without departing from the scope of the invention. Accordingly, it is not intended that the invention be limited, except as by the appended claims.

The invention claimed is:

1. A method of decreasing a surface reactivity of a polymeric stent, said method comprising:
   fabricating a biodegradable polymeric stent using polylactic acid (PLA), the stent having a surface;
   preparing a bath comprising PLA-polyethylene glycol (PEG) diblock copolymers dissolved in acetone, the concentration of the PLA-PEG diblock copolymers dissolved in the acetone being 5% weight/volume; and
   immersing at least part of the biodegradable polymeric stent into a said bath for a period of time;
   wherein the sharp surfaces and/or irregularities on the surface of the biodegradable polymeric stent are reduced or eliminated and thereby decrease the surface reactivity of the polymeric stent.

2. The method of claim 1, wherein the bath further comprises a polyether.

3. The method of claim 2, wherein the polyether is polyethylene glycol.

4. The method of claim 1, wherein the temperature of the bath is below the glass transition temperature of the polymeric stent.

5. The method of claim 1, wherein said polymeric stent is immersed in the bath for about 0.1 seconds.

6. The method of claim 1, wherein said polymeric stent is immersed in the bath for about 0.5 seconds.

7. The method of claim 1, wherein the temperature is below 65° C.

8. The method of claim 1, wherein the bath is at a temperature below 50° C.

9. The method of claim 1, wherein the atmospheric pressure over the bath is controlled.

10. The method of claim 1, wherein the bath further comprises agents capable of reducing the surface tension of said bath.

11. The method of claim 1, wherein the predetermined period of time is sufficient to alter an in vivo lifetime of one or more sections of the stent.

* * * * *